United States Patent

Sakane et al.

Patent Number: 5,109,130
Date of Patent: Apr. 28, 1992

[54] CEPHEM COMPOUND

[75] Inventors: Kazuo Sakane; Kohji Kawabata, both of Kawanishi; Shinya Okuda, Osaka, all of Japan

[73] Assignee: Fujisawa Pharmaceutical Co., Ltd., Osaka, Japan

[21] Appl. No.: 658,866

[22] Filed: Feb. 22, 1991

[30] Foreign Application Priority Data

Feb. 27, 1990 [JP] Japan .................... 2-48797

[51] Int. Cl.$^5$ ................. C07D 501/46; A61K 31/545
[52] U.S. Cl. .................................................. 540/222
[58] Field of Search ......................... 540/222; 514/202

[56] References Cited

U.S. PATENT DOCUMENTS 4,927,818  5/1990  Takaya et al. ...................... 540/222

Primary Examiner—Nicholas S. Rizzo
Attorney, Agent, or Firm—Oblon, Spivak, McClelland, Maier & Neustadt

[57] ABSTRACT

The invention relates to a highly stable antibacterial agent which is crystalline 7β-[2-(5-amino-1,2,4-thiadiazol-3-yl)-2-(1-carboxy-1-methylethoxyimino)acetamido]-3-[3-amino-2-(2-hydroxyethyl)-1-pyrazolio]methyl-3-cephem-4-carboxylate hydrochloride (syn-isomer).

1 Claim, No Drawings

CEPHEM COMPOUND

This invention relates to a novel cephem compound which is of value as an antibacterial agent and finds application in the medical field.

More particularly, this invention relates to crystalline 7β-[2-(5-amino-1,2,4-thiadiazol-3-yl)-2-(1-carboxy-1-methylethoxyimino)acetamido]-3-[3-amino-2-(2-hydroxyethyl)-1-pyrazolio]methyl-3-cephem-4-carboxylate hydrochloride (syn-isomer) [hereinafter referred to briefly as compound (I)].

The free form of compound (I), namely 7β-[2-(5-amino-1,2,4-thiadiazol-3-yl)-2-(1-carboxy-1-methylethoxyimino)-acetamido]-3-[3-amino-2-(2-hydroxyethyl)-1-pyrazolio]methyl-3-cephem-4-carboxylate (syn-isomer) (hereinafter referred to as known compound (II)] is described, for example, in Example 6 (4) of EP0261615A2 and is known to have high antibacterial activity.

However, further experimental investigation by the inventors of this invention revealed that the known compound (II) described in the said EP0261615A2 is an amorphous product and the said amorphous known compound (II) has disadvantages, for example, it is unstable, bulky and not so pure, and therefore it is not so suitable for use as a drug.

The inventors of this invention attempted to improve this known compound (II) and succeeded in developing compound (I) which does not have disadvantages as mentioned above and is more suitable for use as a drug. This invention is predicated on the above-mentioned successful endeavor.

Compound (I) can be produced by reacting known compound (II) with HCl (for example, hydrochloric acid, etc.).

This reaction can be carried out in the presence of the common solvent, such as water or the like.

The reaction temperature is not particularly critical. Thus, generally the reaction can be carried out under cooling or warming.

The following is the result of a comparative stability test conducted for demonstrating the advantage of compound (I) over known compound (II).

| Test samples | |
|---|---|
| Sample 1 | Known compound (II) obtained in Example 6 (4) of EP0261615A2 |
| Sample A | Compound (I) obtained in Example which appears hereinafter |

TEST METHOD

The stability of each test sample in air-tight containers at 50° C. was evaluated. The potency of each sample was determined by liquid chromatography and the residual percentage of each compound was calculated.

| Test sample | Test item | Results Initial value | After 15 days | After 30 days |
|---|---|---|---|---|
| Sample 1 | Potency (residual percentage %) | 100 | 57.5 | 46.3 |
| Sample A | Potency (residual percentage %) | 100 | 99.4 | 99.5 |

It is apparent from the above results that Sample A is more stable than Sample 1.

The following example is further illustrative of the invention.

EXAMPLE

A suspension of 7β-[2-(5-amino-1,2,4-thiadiazol-3-yl)-2-(1-carboxy-1-methylethoxyimino)acetamido]-3-[3-amino-2-(2-hydroxyethyl)-1-pyrazolio]methyl-3-cephem-4-carboxylate (syn-isomer) (10 g) in water (10 ml) is adjusted to pH 1.0 with 2N-hydrochloric acid at 20° C. with stirring. The resulting solution is further stirred at the same temperature for 2 hours and the resultant crystals are collected by filtration and dried to give crystals of 7β-[2-(5-amino-1,2,4-thiadiazol-3-yl)-2-(1-carboxy-1-methylethoxyimino)acetamido]-3-[3-amino-2-(2-hydroxyethyl)-1-pyrazolio]methyl-3-cephem-4-carboxylate hydrochloride (syn-isomer) (6.7 g).

IR (Nujol): 3430, 3250, 1780, 1710, 1645, 1580, 1515 cm$^{-1}$.

NMR (D$_2$O-NaHCO$_3$, δ): 1.53 (6H, s), 3.06 & 3.40 (2H, ABq, J=18 Hz), 3.70–3.96 (2H, m), 4.15–4.46 (2H, m), 5.10 (2H, broad s), 5.23 (1H, d, J=5 Hz), 5.85 (1H, d, J=5 Hz), 5.95 (1H, d, J=5 Hz), 5.95 (1H, d, J=3 Hz), 7.85 (1H, d, J=3 Hz)

mp: 188° C. (dec.)

What we claim is:

1. Crystalline 7β-[2-(5-amino-1,2,4-thiadiazol-3-yl)-2-(1-carboxy-1-methylethoxyimino)acetamido]-3-[3-amino-2-(2-hydroxyethyl)-1-pyrazolio]methyl-3-cephem-4-carboxylate hydrochloride (syn-isomer).

* * * * *